United States Patent
Duflot et al.

(10) Patent No.: US 8,933,219 B2
(45) Date of Patent: Jan. 13, 2015

(54) METHOD FOR DECONTAMINATING STARCH HYDROLYSATES FOR THE PREPARATION OF GLUCOSE POLYMERS FOR PERITONEAL DIALYSIS

(75) Inventors: Pierrick Duflot, La Couture (FR); Damien Passe, Douai (FR); Jean-Marc Verrin, Beuvry (FR)

(73) Assignee: Roquette Freres, Lestrem (FR)

( * ) Notice: Subject to any disclaimer, the term of this patent is extended or adjusted under 35 U.S.C. 154(b) by 84 days.

(21) Appl. No.: 13/883,334

(22) PCT Filed: Nov. 2, 2011

(86) PCT No.: PCT/FR2011/052555
§ 371 (c)(1), (2), (4) Date: May 3, 2013

(87) PCT Pub. No.: WO2012/059685
PCT Pub. Date: May 10, 2012

(65) Prior Publication Data
US 2013/0228168 A1 Sep. 5, 2013

(30) Foreign Application Priority Data
Nov. 3, 2010 (FR) ...................... 10 59060

(51) Int. Cl.
- C08B 30/00 (2006.01)
- C08B 30/04 (2006.01)
- A61K 31/718 (2006.01)
- B01D 61/14 (2006.01)
- C08B 30/18 (2006.01)
- C12P 19/04 (2006.01)
- C12P 19/14 (2006.01)

(52) U.S. Cl.
CPC .............. *C08B 30/04* (2013.01); *A61K 31/718* (2013.01); *B01D 61/14* (2013.01); *C08B 30/18* (2013.01); *C12P 19/04* (2013.01); *C12P 19/14* (2013.01)
USPC .............................. 536/124; 536/102; 127/71

(58) Field of Classification Search
CPC ................................ C08B 30/00; C08B 30/04
USPC ...................................... 536/124, 102; 127/71
See application file for complete search history.

(56) References Cited

U.S. PATENT DOCUMENTS

2010/0024396 A1 * 2/2010 Lupescu et al. ............... 60/284
2010/0273735 A1 10/2010 Deremaux et al.
2012/0046460 A1 * 2/2012 Biguet et al. .................. 536/127

FOREIGN PATENT DOCUMENTS

| WO | WO 2007/099212 | 9/2007 |
| WO | WO 2009/117558 | 9/2009 |
| WO | WO 2010/125315 | 11/2010 |

OTHER PUBLICATIONS

Written Opinion in International Application No. PCT/FR2011/052555, Feb. 3, 2012, pp. 1-10.

* cited by examiner

*Primary Examiner* — Patrick Lewis
*Assistant Examiner* — Everett White
(74) *Attorney, Agent, or Firm* — Saliwanchik, Lloyd & Eisenschenk

(57) ABSTRACT

The subject matter of the invention is a method for decontaminating starch hydrolysates from which glucose polymers for producing peritoneal dialysis solutions will be prepared.

22 Claims, No Drawings

METHOD FOR DECONTAMINATING STARCH HYDROLYSATES FOR THE PREPARATION OF GLUCOSE POLYMERS FOR PERITONEAL DIALYSIS

CROSS-REFERENCE TO RELATED APPLICATION

This application is the U.S. national stage application of International Patent Application No. PCT/FR2011/052555, filed Nov. 2, 2011.

The present invention relates to a method for decontaminating starch hydrolysates from which glucose polymers for producing peritoneal dialysis solutions will be prepared.

For the purposes of the invention, the term "method for decontaminating" is intended to mean a method which makes it possible to rid starch hydrolysates of contaminating microorganisms (live and/or sporulated microorganisms such as yeasts, molds and bacteria) and of substances capable of causing peritonitis (which may or may not be aseptic), a major complication of peritoneal dialysis, these substances possibly being:

lipopolysaccharides (LPSs), which are toxic macromolecular complexes constitutively present in the outer membrane of all Gram-negative bacteria. From a structural point of view, LPSs consist of a lipid A and of a polysaccharide component extending beyond the outer membrane. Lipid A has toxic properties and it corresponds to the endotoxin of Gram-negative bacteria which is released, massively, only after lysis of the bacterium, β-glucans, which are polymers of D-glucose linked via β-glucosidic linkages. β-Glucans are a diversified group of molecules with variable molecular weight, solubility, viscosity and three-dimensional configuration. β-Glucans are in particular constituents of the cell wall of plant cells, of yeasts and of certain molds and bacteria, peptidoglycans (PGs), which are polysaccharide components of the walls of Gram (+) bacteria. Peptidoglycans, also known as mureins, or mucocomplexes, or mucopeptides, are made up of a polysaccharide component and a peptide component. The polysaccharide is a polymer of glycosaminopeptide in which the N-acetylglucosamine and the N-acetylmuramic acid are linked via β-1,4 osidic linkages.

The invention relates more particularly to the modification of the way in which conventional methods for producing starch hydrolysates are carried out, in the sense that filtration steps in series or particular activated carbon treatment steps, optionally coupled to enzymatic treatment steps, are added to said conventional methods.

These additional steps are therefore aimed at guaranteeing the innocuousness of the starch hydrolysates thus prepared, i.e. guaranteeing a content of contaminating substances well below the quantification threshold of the conventional methods for assaying said contaminating substances.

Peritoneal dialysis is a type of dialysis of which the objective is to remove waste such as urea, creatinine, excess potassium or surplus water that the kidneys do not manage or no longer manage to purify out of the blood plasma. This medical treatment is indicated in the event of end-stage chronic renal failure.

It is an intracorporeal purification which uses the peritoneum as a dialysis membrane. Toxic waste from the blood crosses the semi-permeable membrane of the peritoneum, to a solution known as a dialysate. The dialysate is introduced into the peritoneal cavity via a permanent catheter. There are two types of peritoneal dialysis:

CAPD (continuous ambulatory peritoneal dialysis), a treatment which is based on passing through 4 bags of dialysate per day according to medical prescription, APD (automated peritoneal dialysis), a continuous nocturnal treatment which corresponds to approximately 15 liters of dialysate per 8 hours according to medical prescription.

The dialysates most commonly used are composed of a buffer solution (of lactate or of bicarbonate) at pH acid (5.2-5.5) or physiological pH (7.4), to which electrolytes (sodium, calcium, magnesium, chlorine) and an osmotic agent (glucose or a glucose polymer, such as "icodextrin" present in the Extraneal® ambulatory peritoneal dialysis solution sold by the company Baxter) are added.

The electrolytes and the osmotic agent each play a role in the exchange mechanism, according to their respective physicochemical properties:

metabolic waste (such as urea or creatinine) or other overabundant electrolytes that the kidney no longer or insufficiently removes by the urinary tract and the urine will be extracted from the blood plasma by diffusion of the components toward the dialysate, in which the concentration levels of these same components are lower;

the surplus water, that the kidney normally removes in order to regulate plasma volume, will be attracted by osmolarity according to the glucose or glucose polymer concentration in the dialysate: the more concentrated the solution is, the more the water present in the body will be taken up by the dialysate.

The glucose polymer, such as icodextrin mentioned above, is preferred to glucose as osmotic agent because, although glucose has the advantage of being relatively safe and inexpensive, it has a certain number of drawbacks.

Owing to its small size, the glucose which rapidly crosses the peritoneum leads to a loss of osmotic gradient in 2 to 4 hours of infusion.

The ultrafiltration characteristics of peritoneal dialysis solutions are therefore considered to be better if glucose is replaced with high-molecular-weight substances, such as glucose polymers, as will be demonstrated hereinafter.

The standard glucose polymers are produced by acid or enzymatic hydrolysis of starch from cereals or from tuberous plants.

Acid hydrolysis of starch, which is completely random, or enzymatic hydrolysis thereof, which is slightly more ordered, provides mixtures of glucose (monomer) and glucose chains which comprise very short molecules (oligomers), with a low degree of polymerization (or DP), and very long molecules (polymers), with a high DP. Glucose polymers have, moreover, an extremely varied molecular weight.

In the more particular field of the use of glucose polymers for continuous ambulatory peritoneal dialysis, it very quickly became apparent that these starch hydrolysates (mixtures of glucose and of glucose oligomers and polymers) could not be used as such.

European patent application EP 207 676 teaches that glucose polymers forming clear and colorless solutions at 10% in water, having a weight-average molecular weight (Mw) of 5000 to 100 000 daltons and a number-average molecular weight (Mn) of less than 8000 daltons are preferred.

Such glucose polymers also preferably comprise at least 80% of glucose polymers of which the molecular weight is between 5000 and 50 000 daltons, little or no glucose or glucose polymers with a DP less than or equal to 3 (molecular weight 504) and little or no glucose polymers with a molecular weight greater than 100 000 (DP of about 600).

In other words, the preferred glucose polymers are glucose polymers with a low polydispersity index (value obtained by calculating the Mw/Mn ratio).

It is in fact easily imagined for this application that low-molecular-weight monomers or polymers rapidly cross the peritoneal wall and are thus of no long-lasting value for creating an osmotic pressure gradient, and that very high-molecular-weight polymers, which lack osmotic power, are to be avoided and even prohibited since they are potentially dangerous if they come to precipitate subsequent to retrogradation thereof.

The methods proposed in this patent application EP 207 676 for obtaining these glucose polymers with a low polydispersity index from starch hydrolysates consist:

either in carrying out a fractional precipitation of a maltodextrin with a water-miscible solvent, or in carrying out a molecular filtration of this same maltodextrin through various membranes possessing an appropriate cut-off or exclusion threshold.

In the two cases, these methods are aimed at removing at the same time the very high-molecular-weight polymers and the low-molecular-weight monomers or oligomers.

However, these methods do not provide satisfaction both from the point of view of their implementation and from the point of view of the yields and the quality of the products that they make it possible to obtain.

In the interests of developing a method for producing a completely water-soluble glucose polymer with a low polydispersity index preferentially less than 2.5, preferably having an Mn of less than 8000 daltons and having an Mw of between 12 000 and 20 000 daltons, said method lacking the drawbacks of the prior art, the applicant company endeavored to solve this problem in its patent EP 667 356, by starting from a hydrolyzed starch rather than from a maltodextrin.

This method consists in:
subjecting a waxy starch milk to acid hydrolysis to give a DE between 8 and 15;
optionally adding to this acid hydrolysis by means of an enzymatic hydrolysis with bacterial alpha-amylase to give a DE between 11 and 18;
chromatographing this acid-enzyme double hydrolysate on macroporous strong cationic resins in alkali metal or alkaline-earth metal form;
collecting the glucose polymer excluded during this chromatography step.

In that patent, in order to obtain a glucose polymer having a polydispersity index of less than 2.5, the glucose polymer excluded during this chromatography step is collected in a weight yield of about 60% of the starch hydrolysate processed upstream of the chromatography step.

This glucose polymer then preferably contains less than 3% of glucose and of glucose polymers having a DP less than or equal to 3 and less than 0.5% of glucose polymers having a DP greater than 600.

Application WO 2007/099212 also describes a method for preparing glucose polymers suitable for peritoneal dialysis. The method ends with fractionation steps in which the low-molecular-weight fractions are eliminated, in particular those having a molecular weight of less than 9000, while the other fractions, of high molecular weight, are recovered. More specifically, the method comprises a step of treatment with activated carbon (Norit SX+), a fractionation with a cut-off threshold of 9000 daltons, recovery of the retentate, and then a step of demineralization and of treatment with activated carbon (Norit SX+).

It is finally henceforth accepted by experts in the field of peritoneal dialysis that these glucose polymers, used for their osmotic power, are entirely satisfactory.

However, risks of microbial contamination of these preparations intended for peritoneal dialysis are to be deplored.

For example, the catheter implanted in the peritoneal cavity is a portal of entry favorable to microorganisms. The numerous manipulations on the catheter during the infusion and drainage phases increase the risk of local or systemic infection.

Furthermore, an additional contamination risk factor may be directly linked to the impurities that can pollute the glucose polymers used as osmotic agents.

It is in fact known that glucose polymer production circuits can be contaminated with microorganisms, or with pro-inflammatory substances containing said microorganisms.

The contamination of corn or wheat starches with microorganisms of yeast, mold and bacteria type, and more particularly with acidothermophilic bacteria of *Alicyclobacillus acidocaldarius* type (extremophilic bacteria which grow in the hot and acidic zones of the circuit), is, for example, described in the starch industry.

The major risk for the patient which receives these contaminated products is then peritonitis.

Clinical suspicion of peritonitis is diagnosed when there is a cloudy dialysate together with variable clinical manifestations, namely abdominal pain, nausea, vomiting, diarrhea and fever.

These episodes of peritonitis are caused by intraperitoneal bacterial infections, and the diagnosis is usually easily established through positive dialysate cultures.

"Sterile peritonitis", which is also described as aseptic, chemical or culture-negative peritonitis, is for its part typically caused by a chemical irritant or a foreign body.

Since the introduction of icodextrin for the preparation of peritoneal dialysis solutions, isolated cases of aseptic peritonitis have been reported that can be linked to various causes, and in particular induction by pro-inflammatory substances potentially present.

However, these pro-inflammatory substances are not detected by the tests usually carried out in order to determine the innocuousness of such preparations.

The tests described today in the pharmacopeia for detecting pyrogenic substances are in fact the following:

the "LAL" test, for detecting bacterial endotoxins (LPS) which are major components of Gram-negative bacteria, the rabbit pyrogen test, for detecting bacterial endotoxins (LPS) and also β-glucans, which are components of the walls of fungal floras (yeasts and molds).

Although generally reliable, these two tests have their limits.

The rabbit pyrogen test is based on the indirect detection of pyrogenic substances by measuring an elevation in the temperature of the rabbit that has been injected with the product containing these substances (febrile response).

This test can produce false negatives, if the undesirable substance has a biological activity that is too weak or a concentration that is too low to induce a systemic pyrogenic response.

However, this substance may have a biological activity or concentration sufficient to produce a local inflammatory reaction.

The other biological impurities (DNA, etc.) are not detected. The same is true for peptidoglycans, which are major components of the cell membranes of Gram-positive bacteria.

The manifestation of aseptic peritonitis observed with peritoneal dialysis solutions containing icodextrin therefore, for certain cases, attests to the way that some substances can escape the tests described in the pharmacopeia and can be responsible for undesirable clinical effects.

In order to remedy this situation, the company Baxter has proposed making efforts to detect the Gram-positive microbial contaminants in its peritoneal dialysis solutions, or directly on the purified glucose polymers intended to be part of the composition of said peritoneal dialysis solutions.

In particular, in its patent EP 1 720 999, the company Baxter proposes developing a method based on the detection of peptidoglycans.

This detection is then recommended directly on the peritoneal dialysis preparations, or on the purified glucose polymers.

This method consists in carrying out, on the glucose polymers:
- "bioburden" testing for detecting the acidophilic thermophilic Gram-positive microorganism *Alicyclobacillus acidocaldarius*, then
- sterilization of said glucose polymers, then
- a test consisting in adding a reagent capable of reacting with the peptidoglycans so as to induce a serine protease cascade reaction,
- quantification of said peptidoglycans.

In other words, the first step detects the presence of live microorganisms that may have contaminated the glucose polymer purification circuit, the second eliminates them by sterilization and the third detects the peptidoglycans resulting from the cell debris not eliminated by the preceding sterilization step.

If it is determined that the amount of these peptidoglycans sought in the glucose polymers is well below a certain threshold (10 ng/ml of a 7.5% solution of glucose polymer, i.e. 133 ng/g of glucose polymers), these glucose polymers are then used to prepare the actual peritoneal dialysis solution.

In other words, in order to prevent the occurrence of these episodes of aseptic peritonitis, the company Baxter, in its patent EP 1 720 999, proposes testing the production and the use of the peritoneal dialysis solutions by means of a protocol for detecting peptidoglycans in the peritoneal dialysis solution.

The company Baxter has also proposed no fewer than four other methods for detecting or avoiding the presence of peptidoglycans in the components for the production of peritoneal dialysis solutions, or in the peritoneal dialysis solutions as such.

In its international patent application WO 2009/117302, the company Baxter describes the removal of contaminating substances by passing over ion exchange resin.

However, it is to be deplored that this technology is only partially effective, the inventors themselves recognizing that the purpose of this adsorption on resin is "to reduce" the risk of contamination, since it retains only a "portion" of the microbial contaminants present both in the glucose polymers and in the final peritoneal dialysis solution.

It is even recommended to pass the glucose polymers or the peritoneal dialysis solution over several ion exchange resins in series, thereby constituting a particularly laborious decontamination method.

A test for detecting peptidoglycans is, moreover, carried out (IL6 analysis) in order to verify the innocuousness of the solutions thus obtained.

In its international patent application WO 2009/117303, a method for detecting peptidoglycans in the glucose polymers or directly in the peritoneal dialysis preparation is proposed which comprises determining the IL-6 response established as a function of a concentration of pro-inflammatory substance taken as a reference, and establishing a dose/response curve of the IL6 response compared with various concentrations of pro-inflammatory substances.

This method therefore constitutes an improvement of the detection method developed in patent application EP 1 720 999.

However, this method requires using IL6-producing cells isolated from human individuals hypersensitive to particular pro-inflammatory substances, in the case in point to peptidoglycans.

Once again, this diagnostic method makes it possible to reject contaminated batches with great sensitivity, but does not make it possible to prevent said contamination.

In its international patent application WO 2009/117304, it is a question of filtering the glucose polymer solution or the peritoneal dialysis preparation on an ultrafiltration membrane with a cut-off threshold of 30 kDa.

Baxter would thus have established that the contaminant size of between 30 and 100 kDa would more probably be that which causes the aseptic peritonitis, whereas the contaminants of smaller size would have no harmful effect.

The method described by Baxter in that patent application therefore consists in filtering any glucose polymer solution or peritoneal dialysis preparation on this ultrafiltration membrane and testing, using the same detection test as that described in patent application WO 2009/117303, the retentate and the filtrate thus obtained.

The principle is the following: the glucose polymer solutions are eliminated if, after ultrafiltration, the retentate causes a pro-inflammatory reaction and the filtrate does not cause one.

On the other hand, the glucose polymer solutions will be kept if the retentate and the filtrate cause a pro-inflammatory reaction and the filtrate response is greater than the retentate response.

If the retentate and the filtrate cause a pro-inflammatory reaction and the filtrate response is less than the retentate response, the nature of the filtrate response is examined:
- if the filtrate response is greater than or equal to 50% of the retentate response, the solutions are kept,
- if the filtrate response is less than 50% of the retentate response, the solutions are rejected.

However, this method is not satisfactory since it is based on the premise that the fragments of small size are innocuous, and as a result, no technique is proposed for eliminating them.

In its patent application 2009/117558, Baxter acts by means of enzymes for degrading the cell wall components of the microbial contaminants.

These enzymes, such as lysozyme, used in soluble or immobilized form, are employed alone or in combination with other enzymes for degrading microbial contaminants, and the glucose polymer or the dialysis preparation thus treated are tested for their cytokine response.

This enzymatic treatment on the final product or on the dialysis preparation will then actually be prescribed for patients if no cytokine response is detected.

However, once again, nothing is proposed for eliminating the debris of the cell wall components thus hydrolyzed, nor for eliminating the substances which naturally contaminate the enzymatic preparations used.

It results from all the aforementioned that no technical solution for making safe the glucose polymers for the preparation of peritoneal dialysis solutions, or for making safe the peritoneal dialysis solution as such, is completely satisfactory.

The applicant company, to its credit, has found that the solution must be based first and foremost on controlling the quality of the raw material used for preparing the glucose polymers for the preparation of peritoneal dialysis solutions, i.e. proposed a simple and effective method for removing the contaminants of starch hydrolysates as such.

In other words, it is a question of acting on the problem of contamination at its source, and not only on the final products or on the final peritoneal dialysis solution.

The present invention therefore relates to a method for preparing glucose polymers for producing peritoneal dialysis solutions, which method comprises decontaminating the starch hydrolysates from which said glucose polymers will be prepared.

This decontamination aims to guarantee the production of starch hydrolysates which should not have residual contaminants, i.e. to guarantee contents less than or equal to the following values, i.e.:

for live microorganisms: total mesophilic flora: <50 g/g; molds and yeasts: <15 g/g; acidothermophilic Bacilli: <10 g/g;

for endotoxins (LPS) and β-glucans, via the LAL test (gel-clot endpoint method) using reagents produced by Charles River-Endosafe (LAL lysate of sensitivity 0.015 E.U/ml ref. OR15015 and CSE endotoxins 500 ng or 10 ng per bottle ref. E110 or E120); <0.6 EU/g;

for peptidoglycans and β-glucans via a high-sensitivity test developed by the applicant company: <8 ng/g of glucose polymers.

The expression "high-sensitivity test developed and validated by the applicant company" is intended to mean a test developed and validated by the applicant company by adapting the SLP-HS single set kit ref. 293-58301 produced and sold by the company Wako Pure Chemical Industries Ltd.

This test consists in using the "SLP-HS" (Silkworm Larvae Plasma-High sensitivity) reagent, said reagent being prepared from the silkworm larvae plasma, capable of:

reacting with the peptidoglycans and β-glucans contained in a solution of glucose polymer prepared at 5% in water (special water for LAL test, for example), inducing a serine protease cascade reaction, and detecting and/or quantifying said peptidoglycans and β-glucans by means of a Toxinometer tube reader manufactured and sold by the company Wako Pure Chemical Industries Ltd. at very low thresholds, i.e.:

a limit of detection (LD) at a threshold of approximately 0.05 ng/ml (i.e. 1 ng/g of glucose polymer) and a limit of quantification (LQ) at a threshold of approximately 0.15 ng/ml (3 ng/g of glucose polymer)

(LD and LQ determined in the glucose polymer product tested).

More specifically, the SLP-HP test consists in:

preparing the test glucose polymer in solution at 5% in water of appropriate quality (special water for LAL test for example), producing a calibration range of peptidoglycans in water over the application range of from 0.04 to 2.5 ng/ml (target values) with the peptidoglycan standard (extracted from *Staphylococcus aureus*) of the SLP-HS single set kit for establishing a straight calibration line (logarithmic-scale linear regression Ta=f (PG content)), introducing 100 µl of the test solution prepared into the HS-SLP tube after reconstitution by adding 100 µl of the diluent (supplied in the abovementioned kit), introducing the SLP-HS tube into the incubation well of the Toxinometer tube reader (Wako Pure Chemical Ltd.) thermostatted at 30° C. and parameterized according to the conditions recommended by the manufacturer, the PG content of the test solution being calculated by means of the straight calibration line established.

The result is expressed in ng/ml of a solution of 5% tested then in ng/g of glucose polymer.

In a first preferential mode of the method in accordance with the invention, said method for decontaminating a starch hydrolysate, for the preparation of glucose polymers for peritoneal dialysis, is characterized in that it comprises the following steps:

1) preparing a starch hydrolysate, 2) filtering said starch hydrolysate so as to remove any contaminant having the size of a microorganism of yeast, mold or bacteria type, 3) treating said starch hydrolysate from which the contaminating microorganisms have thus been removed, i.e. the filtrate, with enzymes for degrading the cell wall polysaccharide constituents, chosen from the group consisting of lysozyme and laminarinase, preferably laminarinase, 4) ultrafiltering the starch hydrolysate thus enzymatically treated, 5) treating the resulting starch hydrolysate on activated carbon with a high adsorption capacity, 6) collecting the starch hydrolysate thus decontaminated.

In the first step of this first variant of the method in accordance with the invention, the starch hydrolysate can be prepared:

either by conventional enzymatic or chemical hydrolysis of the starch from various plant sources, such as wheat, corn, potato, pea, rice, cassava, etc., so as to achieve a dextrose equivalent (DE) of less than 20, characteristic of maltodextrins, or by acid hydrolysis of a waxy starch milk to give a DE between 8 and 15, with the optional addition of an enzymatic hydrolysis using bacterial alpha-amylase to give a DE between 11 and 18, according to the teaching of patent EP 667 356 mentioned above.

In order to test the soundness of its decontamination method, as will be explained hereinafter, the applicant company has hydrolysates of corn starch or maltodextrins which are optionally artificially contaminated:

with the 4 categories of contaminants presented above, with peptidoglycans (in free form or bound form, i.e. bound at the surface of live cells) with or without endotoxins, with β-glucans and peptidoglycans, with or without endotoxins.

In the second step of this first variant of the method in accordance with the invention, the microorganisms capable of contaminating said starch hydrolysates, i.e. yeasts, molds and bacteria, and in particular the acidothermophilic bacteria of *Alicyclobacillus acidocaldarius* type, are removed, their size being greater than the filtration pore diameters.

Any method known per se to those skilled in the art is usable, but the applicant company recommends carrying out:

either a sterilizing filtration which consists principally of a membrane filtration where the pore diameter is 0.22 µm, preceded, where appropriate, by a membrane prefiltration where the pore diameter is 0.45 µm.

The filtration is carried out using several cartridge filters inserted into a vertical casing toward which the starch hydrolysate is directed. These cartridge filters are supplied by the companies Pall or Millipore. The size of the cartridges may be 10, 20 or 30 inches, and the number of cartridges installed makes it possible to obtain a filtration surface area sufficient to pass a product flow rate of between 1 and 20 l/minutes/m².

These cartridge filters have resistance capacities for continuous working at high temperature, of about 75° C., and for passing the abovementioned flow rate for a period of time greater than 700 h. Working at a temperature of 75° C. makes it possible to limit any microbiological growth, in particular growth of thermophilic flora.

Their temperature resistance also makes it possible to carry out a sterilization before they are brought into service. This sterilization consists in passing steam at 2 bar through the casing for a period of 20 minutes. This sterilization is followed by rinsing with purified water for a period of 5 minutes.

These filters also have capacities to withstand certain chemical products used for equipment cleaning, and in particular peracetic acid at a concentration of 5%.

An integrity test can be carried out on these cartridges using an integritest from the company Millipore, for example. This integrity test is carried out when the cartridges are installed in order to verify the assembly thereof. This test is then carried out before each cleaning of the equipment and, finally, before the disassembling in order to validate the correct functioning of said cartridges during the production phase.

The working pressure difference (ΔP) of these filters must not exceed 2 bar in order to guarantee their integrity. Should this be the case, these filters must be replaced with new ones;
   or an ultrafiltration on a membrane having a cut-off threshold of 300 000 Da.

The cut-off threshold is thus chosen so as to retain any cell contaminants in the retentate.

The cut-off threshold makes it possible to retain the microorganisms, i.e. yeasts, molds and bacteria, and in particular the acidothermophilic bacteria of *Alicyclobacillus acidocaldarius* type.

The surface of the filter is determined as a function of the nature of the fluid and of the flow rate to be treated.

The ultrafiltration membranes may be of ceramic or organic type. Since these two types of membrane have a different resistance to temperature and to chemical products, membranes of ceramic type, which make it possible to work at temperatures above 75° C., will be preferred.

Their temperature resistance makes it possible to carry out a steam sterilization before they are brought into service. This sterilization consists in passing steam at 2 bar through the housing for a period of 20 minutes. This sterilization is followed by rinsing with purified water for a period of 20 minutes.

It is also advisable to work at a temperature of about 75° C. in order to avoid any microbiological growth.

These filters also have capacities to withstand certain chemical products used for equipment cleaning, and in particular peracetic acid at a concentration of 5% and sodium hydroxide at a concentration of 1%.

The starch hydrolysate feed pressure is between 2 and 20 bar and is adjusted by the pump feeding this module. When the maximum pressure is reached but the flow rate of the starch hydrolysate is too low, the membranes should be cleaned with sodium hydroxide so that they return to full efficiency.

The monitoring of the drop in the level of contaminants can be analyzed by taking periodic samples from the permeate.

The microorganisms will be considered to have been efficiently removed if the samples taken from the filtrate show a level below the threshold of quantification of conventional assaying methods.

In the third step of this first variant of the method in accordance with the invention, said starch hydrolysate from which the contaminating microorganisms have thus been removed is treated with enzymes for degrading the cell wall polysaccharide constituents, chosen from the group consisting of lysozyme and laminarinase, preferably laminarinase.

After the removal of the live microorganisms, this step thus makes it possible to remove the residual toxic molecules (released by the microorganisms or else present in the cell membrane debris).

These enzymes for degrading the cell wall polysaccharide constituents are chosen so as to break the membranes of the two major contaminating microorganisms of the starch hydrolysates (yeasts and gram (+) bacteria) which might have escaped the preceding filtration step, and especially for hydrolyzing their β-glucans and peptidoglycans which may be in free form in said starch hydrolysates.

Laminarinase has an endo-β-1,3-glucanase (EC 3.2.1.6) activity, which destroys the cell wall of yeasts and of certain molds.

Lysozyme, acid hydrolase (EC 3.2.1.17), destroys the bacterial wall of gram (+) bacteria by catalyzing the hydrolysis of the constituent glycosaminoglycans of said wall. It hydrolyzes the covalent bonds between the N-acetylmuramic acid and the 4th carbon atom of N-acetylglucosamine of peptidoglycans. The bacterial wall peptidoglycan "backbone" is in fact a copolymer consisting of the covalent linking of these two molecules, in alternation, to which are attached peptides which bridge the polymer chains.

These enzymes are introduced into the starch hydrolysates at the concentration of 0.001% to 1% on a dry weight basis of starch hydrolysates, preferably between 0.1% and 0.5%.

The laminarinase is used on the starch hydrolysates at 10% of dry mass at a temperature of 50° C., at a pH of 4.6, for 5 to 24 hours, preferably for 20 hours, as will be exemplified hereinafter.

The lysozyme is, for its part, used on the starch hydrolysates at 10% of dry matter at a temperature of 37° C., at a pH of 7, for 5 to 24 hours, preferably for 20 hours, as will be exemplified hereinafter.

In the fourth step of this first variant of the method in accordance with the invention, a tangential ultrafiltration of the starch hydrolysate thus enzymatically treated is carried out.

The cut-off threshold of the ultrafiltration membrane is chosen so as to retain any β-glucans and peptidoglycan degradation products in the retentate and especially makes it possible to retain the enzymes used in the preceding step.

The ultrafiltration membrane then has a cut-off threshold of between 20 000 and 50 000 daltons, preferably about 30 000 daltons.

In the fifth step of this first variant of the method in accordance with the invention, the resulting starch hydrolysate, i.e. the permeate or filtrate, is passed through activated carbon with a high adsorption capacity.

The applicant company recommends taking quite particular care in carrying out this activated carbon treatment step, which constitutes a key step of this first variant of the method in accordance with the invention.

The applicant company has in fact found that the choice of an appropriate quality of the activated carbon to be used in this finishing step conditions the virtual absence of contaminants capable of being detected in the starch hydrolysates thus treated ("virtual" being understood to mean concentrations well below the threshold of quantification of the conventional assaying methods).

It is known to those skilled in the art that activated carbon is an adsorbent inert carbon-based material consisting of a porous network which develops a considerable surface area that can reach up to 1500 m² per gram of material (the pore diameters ranging between 4 and 100 000 Angstroms).

In order to be effective, an activated carbon must therefore have a certain internal surface area developed within the porous structure onto which the impurities that it is desired to remove will adsorb.

In order to model this adsorption capacity, those skilled in the art usually describe the adsorption process by means of an adsorption isotherm (Langmuir isotherm, Langmuir-Hinshelwood isotherm, BET isotherm or Freundlich isotherm).

The adsorption isotherm is a curve which represents the amount of impurities adsorbed per unit mass of activated carbon as a function of the residual concentration of the impurities in solution.

In order to construct this isotherm, known and increasing amounts of activated carbon are introduced into a volume of solution to be treated and, after a given contact time, the residual concentration of impurities adsorbed is measured.

The applicant company therefore recommends, as a preliminary to any use of an activated carbon intended here to end the decontamination of the starch hydrolysates for the preparation of glucose polymers for peritoneal dialysis (fifth finishing step), to precisely chose the quality of the activated carbon by modeling its adsorption isotherm.

A preliminary test is thus carried out in order to choose the most efficient activated carbon, which test consists in plotting the Freundlich adsorption isotherm for various qualities of activated carbon which are commercially available (or even to test various batches of one and the same type of activated carbon), in comparison with their capacity to adsorb known amounts of contaminants of bacterial endotoxin and peptidoglycan type which are here taken as references.

It is therefore a question of carrying out a precise qualification of all the batches intended to be used in this key starch hydrolysate finishing step.

The applicant company recommends testing more particularly here the quality of "meso" type, i.e. having a high methylene blue number, or the quality of "micro" type, i.e. having a high iodine number.

Thus, the method may comprise a prior step of determining the adsorption isotherm of several activated carbons, in particular one of "meso" type and one of "micro" type, and of selecting the most appropriate activated carbon.

The adsorption isotherm which conventionally makes it possible to determine the specific surface area of a given activated carbon will therefore here contribute to assisting the choice of the activated carbon which will make it possible:
  to adsorb all the β-glucan and peptidoglycan degradation products generated during the preceding steps, regardless of their size,
  and especially to adsorb the endotoxins capable of contaminating the starch hydrolysates, and also the endotoxins introduced by the enzymes used (no commercially available industrial preparation of these enzymes is unfortunately devoid thereof).

As will be exemplified hereinafter, the procedure for determining the Freundlich adsorption isotherm recommended by the applicant company consists in mixing the starch hydrolysate entering with each batch of activated carbon (5 increasing amounts between 0.125% and 2% relative to the dry matter to be treated, i.e. 0.125%, 0.25%, 0.5%, 1% and 2%) at a temperature of 75° C. for one hour.

The temperature of 75° C. is the conventional working temperature of the commercially available activated carbons, validated for the adsorption kinetics.

The period of one hour of contact time was determined so as to dispense with the kinetic constraint relative to the thermodynamics of the system.

As for the pH, it is fixed at a value of 4.5, since the applicant company has determined that, in order to ensure optimum adsorption of the peptidoglycan and endotoxin impurities, it is necessary, beforehand, to condition the starch hydrolysate sample at an acid pH value, i.e. about 4.5.

As will be exemplified hereinafter, the quality of the activated carbon for this fifth finishing step has been identified as an activated carbon of "micro" type, with a high iodine number.

An activated carbon of Norit® SX+ type, sold by the company Norit, is entirely suitable for this quality.

In the final step of this first preferential mode of the method in accordance with the invention, the starch hydrolysate obtained is then collected, and its content of contaminants is analyzed.

In a second preferential mode of the method in accordance with the invention, the method for decontaminating a starch hydrolysate for the preparation of glucose polymers for peritoneal dialysis is characterized in that it comprises the following steps:
  1) preparing a starch hydrolysate,
  2) filtering said starch hydrolysate so as to remove any contaminant having the size of a microorganism of yeast, mold or bacteria type,
  3) treating said starch hydrolysate, i.e. the filtrate, so as to remove any contaminant having the minimum size of 50 Angstroms by means of a technique chosen from the group consisting of activated carbon, frontal microfiltration or tangential ultrafiltration,
  4) treating the resulting starch hydrolysate on activated carbon with a high adsorption capacity,
  5) collecting the starch hydrolysate thus decontaminated.

In this second preferential mode of the method in accordance with the invention, the first two steps are identical to those previously described in the first preferential mode presented above.

In the third step of this second preferential mode of the method in accordance with the invention, the starch hydrolysate from which the microorganisms capable of contaminating it have been removed is treated by means of a technique chosen from the group consisting of activated carbon, frontal microfiltration or tangential ultrafiltration.

This step is carried out so as to remove all the high-molecular-weight polysaccharides of bacterial, yeast or mold origin (LPSs, β-glucans, peptidoglycans).

Treatment with activated carbon can be chosen as first technique.

In the same way as described above, the applicant company recommends choosing the quality of activated carbon which is most efficient for carrying out this step of removing the large impurities (debris from live cells of endotoxin type), by means of determining its adsorption isotherm.

Thus, the method can comprise a prior step of determining the adsorption isotherm of several activated carbons, in particular one of "meso" type and one of "micro" type, and of selecting the most appropriate activated carbon.

As will be exemplified hereinafter, the quality of the activated carbon for this final step has been identified as an activated carbon of "meso" type.

An activated carbon of ENO-PC type, sold by the company Ceca, is entirely suitable for this quality.

Moreover, since it has pores with diameters between 15 and 100 Angstroms (called "mesopores"), this activated carbon also makes it possible to retain the high-molecularweight molecules (a porosity of 100 Angstroms makes it possible to retain molecular weights of about 20 kDa).

Treatment by frontal microfiltration can be chosen as second technique.

Frontal microfiltration is a method of filtration which consists in passing the liquid to be filtered through perpendicular to the surface of the filter.

There are conventionally 3 types of frontal microfiltration:
"neutral" frontal filtration, having a cut-off threshold of 0.45 µm, with a neutral surface charge,
anionic frontal filtration, also having a cut-off threshold of 0.45 µm, with positive surface charges, therefore exchanges negatively charged molecules,
cationic frontal filtration, again having a cut-off threshold of 0.45 µm, with negative surface charges, therefore exchanges positively charged molecules.

The applicant company recommends carrying out a frontal filtration, by means of a filtration system with a plus Zeta potential (peptidoglycans having a negative charge at pH 7), of a solution of starch hydrolysates diluted to 10% of dry matter.

Treatment by tangential ultrafiltration can be chosen as third technique.

Tangential ultrafiltration is conventionally a method of filtration in which the driving force is the pressure of the liquid to be treated.

The pressurized liquid between the module and the liquid produced (called filtrate or permeate) crosses the barrier constituted by the membrane.

The substances retained can be removed from the module in batchwise or continuous mode, depending on the system used, in the concentrate or in a backwashing effluent.

The cut-off threshold is, in the method in accordance with the invention, about 30 000 Da, which enables very small particles to be retained.

The porous structure of the membranes used has a filtering layer of very fine thickness, where the smallest pores are located, whereas the rest of the thickness (more than 100 µm), or support layer, has pores of about a few microns which ensure easy passage of the filtrate and give the assembly mechanical strength.

A surface filtration and not a deep filtration is thus carried out.

The applicant company recommends carrying out a batchwise mode tangential ultrafiltration of a solution of starch hydrolysates diluted to 10% of dry matter, at pH 4.5 at a temperature of 60° C., on a Pall Centramate organic cartridge membrane with a cut-off threshold of 30 000 Da, so as to achieve a volume concentration factor of about 10.

In the fourth step of this second preferential mode of the method in accordance with the invention, the finishing treatment of this decontamination method is carried out by means of activated carbon.

Analysis of the adsorption capacities of the activated carbons used has led the applicant company to preferentially couple, for the starch hydrolysate treatment, two types of activated carbon, of "meso" then "micro" type, in the case where the third step of this second preferential mode according to the invention already consists of an activated carbon treatment step.

This second treatment with "microporous" activated carbon acts as a finishing treatment which makes it possible to rid the starch hydrolysates of all their residual contaminants.

This finishing step, as will be exemplified hereinafter, is also carried out after the prior frontal microfiltration or tangential ultrafiltration treatment, with the same purpose.

In the final step of this first variant of the method in accordance with the invention, the starch hydrolysate obtained is then collected, and its content of contaminants is analyzed.

Thus, in one particular embodiment of this second preferential mode, the method comprises the following steps:
1) preparing a starch hydrolysate,
2) filtering said starch hydrolysate so as to remove any contaminant having the size of a microorganism of yeast, mold or bacteria type,
3) treating said starch hydrolysate, i.e. the filtrate, so as to remove any contaminant having the minimum size of the 50 Angstroms by means of a tangential ultrafiltration, preferably with a cut-off threshold of about from 20 000 Da to 50 000 Da, preferably 30 000 Da,
4) treating the resulting starch hydrolysate, i.e. the filtrate, on activated carbon with a high adsorption capacity, preferably of "micropore" type, such as Norit SX+; and
5) collecting the starch hydrolysate thus decontaminated.

Thus, in another particular embodiment of this second preferential mode, the method comprises the following steps:
1) preparing a starch hydrolysate,
2) filtering said starch hydrolysate so as to remove any contaminant having the size of a microorganism of yeast, mold or bacteria type,
3) treating said starch hydrolysate, i.e. the filtrate, so as to remove any contaminant having the minimum size of 50 Angstroms by means of a treatment on activated carbon, in particular of "mesopore" or "micropore" type, preferably of "mesopore" type, such as one of ENO-PC type;
4) treating the resulting starch hydrolysate on activated carbon with a high adsorption capacity, preferably of "micropore" type, such as Norit SX+; and
5) collecting the starch hydrolysate thus decontaminated.

The invention also relates to the starch hydrolysate capable of being decontaminated by means of the methods, this starch hydrolysate being chosen from the group consisting of enzymatic or acid hydrolysates of starch and of maltodextrins.

Finally, the invention relates to the use of this starch hydrolysate for the preparation of glucose polymers for producing peritoneal dialysis solutions.

The invention will be understood more clearly by means of the examples which follow, which are meant to be nonlimiting illustrations.

EXAMPLE 1

Preparation of the Starch Hydrolysate in Accordance with the Teaching of Patent EP 667 356

The raw material for obtaining the glucose polymers according to the invention is produced from waxy corn starch in the following way:
cleaning of the corn so as to keep exclusively the whole corn grains,
steeping of the corn thus cleaned, in the presence of lactic acid so as to soften the grains,
wet milling, then separation of the various constituents, i.e. germ, cellulose husk, proteins and starch,
cleaning of the starch in countercurrent mode with disinfected water so as to purify the starch both physico-chemically and bacteriologically,
centrifugation and drying of the starch,
suspension of the starch in disinfected water at a final dry matter content of 40% and at a temperature of 45° C. to 50° C., acidification of the starch suspension by addition of HCl at a pH<2, and raising of the temperature to 115 to 120° C. for 6 to 8 minutes, flocculation of the proteins and of the fats at this pH, neutralization of the suspension at pH 5, filtration of the suspension through diatomaceous earth (so as to retain the residual proteins, fats and cellulose), demineralization on strong cationic resin and weak anionic resin, discoloration on standard activated carbon, spray-drying of the concentrated solution in an MSD-type spray dryer sold by the company Niro.

Particularly contaminated batches referenced "A-5250" and "B-3063" were chosen separately in order to test the validity of the methods in accordance with the invention (more or less difficult to decontaminate depending on the nature and on the size of these various peptidoglycan, β-glucan and endotoxin contaminants).

The following table I gives the nature of the contaminants identified in these various batches.

By way of comparison, the nature of the contaminants that it is possible to find in six batches of commercial maltodextrins "C" is also given.

These various batches therefore offer three options for possible contamination:

6 batches "A-5250" essentially contaminated with peptidoglycans (polysaccharides in free form) and β-glucans, 6 batches "B-3063" essentially contaminated with peptidoglycans (live cells or polysaccharides in free form) and endotoxins, with no trace of β-glucans, 6 batches "C", the contamination profile of which is broad-spectrum, i.e. containing all the categories of contaminants.

EXAMPLE 2

Choice of the Qualities of Activated Carbon According to the Nature and the Amount of the β-Glucan and Peptidoglycan Contaminants that May be Found in the Starch Hydrolysates of Batches A-5250 and B-3063 and of a Commercial Maltodextrin C As indicated above, the activated carbon treatment steps are especially carried out in order to adsorb the cell debris of endotoxin, β-glucan and peptidoglycan type.

TABLE I

| Starch hydrolysates | *Alicyclobacillus acidocaldarius* (number of microorganisms on 1 g) | Yeasts (number of microorganisms on 1 g) | Endotoxins + β-glucans (EU/g) | Peptidoglycans (ng/g) | β-Glucan/ Endotoxin distribution (%) |
|---|---|---|---|---|---|
| Methods of measurement | | | LAL test | High-sensitivity test | Modified LAL test |
| Batch "A-5250" No. 1 | 0 | <5 | 9.6 | 2462 | 90/10 |
| Batch "A-5250" No. 2 | 0 | <5 | 19.2 | 2576 | 90/10 |
| Batch "A-5250" No. 3 | 0 | <5 | 9.6 | 1882 | 90/10 |
| Batch "A-5250" No. 4 | 0 | <5 | 4.8 | 3166 | 90/10 |
| Batch "A-5250" No. 5 | 0 | <5 | 9.6 | 2277 | 90/10 |
| Batch "A-5250" No. 6 | 0 | <5 | 9.6 | 3540 | 90/10 |
| Batch "B-3063" No. 1 | 150 | <5 | 2.4 | 36 029 | 0/100 |
| Batch "B-3063" No. 2 | 150 | <5 | 2.4 | 25 029 | 0/100 |
| Batch "B-3063" No. 3 | 150 | <5 | 9.6 | 27 260 | 0/100 |
| Batch "B-3063" No. 4 | 150 | <5 | 1.2 | 10 241 | 0/100 |
| Batch "B-3063" No. 5 | 150 | <5 | 2.4 | 55 691 | 0/100 |
| Batch "B-3063" No. 6 | 160 | <5 | 2.4 | 46 367 | 0/100 |
| Batch "C" No. 1 | 2 | <5 | 9.6 | 13 660 | 75/25 |
| Batch "C" No. 2 | 2 | <5 | 3.6 | 9374 | 75/25 |
| Batch "C" No. 3 | 2 | <5 | 9.6 | 10 556 | 75/25 |
| Batch "C" No. 4 | 2 | <5 | 4.8 | 9353 | 75/25 |
| Batch "C" No. 5 | 2 | <5 | 9.6 | 11 920 | 75/25 |
| Batch "C" No. 6 | 2 | <5 | 9.6 | 16 288 | 75/25 |

The choice of the quality of activated carbon is based on the analysis of the Freundlich isotherms plotted for each activated carbon directly on the starch hydrolysate to be decontaminated.

As will be demonstrated below, the choice of the activated carbon will depend directly on the load of contaminants (in terms of nature and amount) present in the starch hydrolysates to be treated.

As indicated above, the procedure for determining the Freundlich adsorption isotherm consists in mixing the starch hydrolysate (at 10% of dry matter) with each type of activated carbon (5 increasing amounts between 0.125% and 2% relative to the dry matter to be treated, i.e. 0.125%, 0.25%, 0.5%, 1% and 2%) at a temperature of 75° C. for one hour at a pH of 4.5.

The relative efficiency of the activated carbons of "meso" and "micro" type is then determined according to the nature of the contaminants of each batch, by measuring the amount of impurities adsorbed per unit mass of activated carbon as a function of the residual concentration (after one hour of reaction) of the impurities in solution.

2.1 Determination of the Freundlich Isotherms of Activated Carbons of Norit SX+ and ENO-PC Type Compared with Two Batches A-5250

All the batches A have a similar profile: essentially contaminated with peptidoglycans (polysaccharides in free form) and β-glucans.

The following table II gives, for 5 increasing amounts of activated carbon, the residual levels of β-glucans and residual peptidoglycans of batches A-5250 No. 1 and No. 2 of example 1, after treatment with the two qualities of activated carbon.

TABLE II

| | Batch No. 1 Norit SX+ | | Batch No. 2 ENO-PC | |
|---|---|---|---|---|
| Amount of activated carbon | LAL detection method (EU/g) | Peptidoglycan high-sensitivity test (ng/g) | LAL detection method (EU/g) | Peptidoglycan high-sensitivity test (ng/g) |
| 0 | 9.6 | 2462 | 19.2 | 2576 |
| 0.125 | 1.2 | 555 | 0.3 | 416 |
| 0.25 | 0.3 | 127 | 0.3 | 156 |
| 0.5 | 0.3 | 10 | <0.3 | 113 |
| 1 | 0.3 | <1 | <0.3 | 13 |
| 2 | <0.3 | <1 | <0.3 | <1 |

If the adsorption curves for the peptidoglycans (responsible for aseptic peritonitis) taken here as a reference are analyzed, it is observed that:

The adsorption curve for the activated carbon Norit SX+, plotting $$y = \frac{(Co - C)}{(\text{amount of carbon})} = f(C)$$

where
Co=initial amount of contaminants
C=amount of residual contaminants
is reflected by the mathematical equation:
y=2588 $x^{0.2771}$ with a correlation coefficient $r^2$ of 0.9914.
The adsorption curve for ENO-PC is, for its part, reflected by the equation:

$$Y = 1045 \cdot x^{0.4156}$$

with an $r^2$ (correlation coefficient) of 0.9190.

The linearity of these two curves taken separately clearly reflects the efficiency of adsorption of the peptidoglycans by these two qualities of activated carbon.

However, when comparing the two equations, it appears that:
for an amount "x" of peptidoglycans for example of 2000 ng/g, the relative efficiency of the Norit/ENO-PC activated carbon quality is 86%; whereas
for an amount "x" of peptidoglycans for example of 10 ng/g, the relative efficiency of the Norit/ENO-PC activated carbon quality is 180%.

It is deduced from this that the ENO-PC "mesopore" quality is very suitable for the adsorption of large amounts of peptidoglycan contaminants, and that the Norit SX+ "micropore" quality is very suitable for the adsorption of small amounts of residual peptidoglycans.

This result makes it possible, for batch A-5250, to define the order of use of the activated carbons in the steps for decontaminating this particular batch of starch hydrolysate: a step of treatment with ENO-PC activated carbon followed by a step of treatment with Norit SX+ activated carbon.

2.2 Determination of the Freundlich Isotherms of the Activated Carbons of Norit SX+ and ENO-PC Type Compared with Two Batches B-3063

All the batches B have a similar profile: essentially contaminated with peptidoglycans and endotoxins.

The following table III gives, for 5 increasing amounts of activated carbon, the residual levels of β-glucans and residual peptidoglycans of batch B-3063 No. 1 and No. 2 of example 1, after treatment with the two qualities of activated carbon.

TABLE III

| | Batch No. 1 Norit SX+ | | Batch No. 2 ENO-PC | |
|---|---|---|---|---|
| Amount of activated carbon | LAL detection method (EU/g) | Peptidoglycan high-sensitivity test (ng/g) | LAL detection method (EU/g) | Peptidoglycan high-sensitivity test (ng/g) |
| 0 | 2.4 | 36029 | 2.4 | 25 029 |
| 0.125 | 0.5 | 140 | 0.3 | 928 |
| 0.25 | <0.3 | 50 | <0.3 | 300 |
| 0.5 | <0.3 | 10 | <0.3 | 83 |
| 1 | <0.3 | <1 | <0.3 | 10 |
| 2 | <0.3 | <1 | <0.3 | 5 |

If the adsorption curves for the peptidoglycans (responsible for aseptic peritonitis) are analyzed, it is observed that:

The adsorption curve for the Norit SX+ activated carbon is reflected by the mathematical equation:
y=32543 $x^{0.4088}$ with a correlation coefficient $r^2$ of 0.9711.
The adsorption curve for ENO-PC is, for its part, reflected by the equation:

$$Y = 6543 \cdot x^{0.4849}$$

with an $r^2$ (correlation coefficient) of 0.9813.

The linearity of these two curves taken separately clearly reflects the efficiency of adsorption of the peptidoglycans by these two qualities of activated carbon.

However, when comparing the two equations, it appears that:
for an amount "x" of peptidoglycans for example of 2000 ng/g, the relative efficiency of the Norit/ENO-PC activated carbon quality is 279%; whereas for an amount "x" of peptidoglycans for example of 10 ng/g, the relative efficiency of the Norit/ENO-PC activated carbon quality is 417%.

It is deduced from this that the ENO-PC "mesopore" quality is not suitable for the adsorption of peptidoglycans of this batch B-3063, and that the Norit SX+ "micropore" quality can be used here for the adsorption of small and large amounts of peptidoglycans.

This result makes it possible, for batch B-3063, to define the order of use of the activated carbons in the steps for decontaminating this particular batch of starch hydrolysate: in this case, two steps of activated carbon of Norit SX+ type in series.

2.3 Determination of the Freundlich Isotherms of the Activated Carbons of Norit SX+ and ENO-PC Type Compared with Two Batches C The following table IV gives, for 5 increasing amounts of activated carbon, the residual levels of β-glucans/endotoxins and residual peptidoglycans of batches C No. 1 and No. 2 of example 1, after treatment with the two qualities of activated carbon.

TABLE IV

| | Batch No. 1 Norit SX+ | | Batch No. 2 ENO-PC | |
|---|---|---|---|---|
| Amount of activated carbon | LAL detection method (EU/g) | Peptidoglycan high-sensitivity test (ng/g) | LAL detection method (EU/g) | Peptidoglycan high-sensitivity test (ng/g) |
| 0 | 9.6 | 13 660 | 9.6 | 9374 |
| 0.125 | 1.2 | 775 | 1.2 | 896 |
| 0.25 | <0.3 | 190 | 0.6 | 369 |
| 0.5 | <0.3 | 25 | <0.3 | 106 |
| 1 | <0.3 | 10 | <0.3 | 26 |
| 2 | <0.3 | <1 | <0.3 | 28 |

If the adsorption curves for the peptidoglycans (responsible for aseptic peritonitis) are analyzed, it is observed that:

The adsorption curve for the Norit SX+ activated carbon is reflected by the mathematical equation:

$y = 6377 \, x^{0.4132}$ with a correlation coefficient $r^2$ of 0.9874.

The adsorption curve for the ENO-PC is, for its part, reflected by the equation:

$$Y = 783.97 \cdot x^{0.6559}$$

with an $r^2$ (correlation coefficient) of 0.9353.

The linearity of these two curves taken separately clearly reflects the efficiency of adsorption of the peptidoglycans by these two qualities of activated carbon.

However, when comparing the two equations, it appears that:

for an amount "x" of peptidoglycans for example of 2000 ng/g, the relative efficiency of the Norit/ENO-PC activated carbon quality is 128%; whereas for an amount "x" of peptidoglycans for example of 10 ng/g, the relative efficiency of the Norit/ENO-PC activated carbon quality is 2349%.

It is deduced from this that the ENO-PC "mesopore" quality is not suitable for the adsorption of the peptidoglycans of these batches C, and that the Norit SX+ "micropore" quality can be used here for the adsorption of small and large amounts of peptidoglycans.

EXAMPLE 3

Method for Decontaminating the Starch Hydrolysate Using Lysozyme or Laminarinase, Followed by a Step of Ultrafiltration then of Activated Carbon Batches A-5250 No. 3 and No. 5, batches B-3063 No. 3 and No. 5, and the batches of commercial maltodextrins C No. 3 and No. 5 are chosen here.

While it is relatively easy to remove the microorganisms of *Alicyclobacillus acidocaldarius* and yeast type on a 0.2 μm microfiltration module or on an ultrafiltration module with a cut-off threshold of 300 kDa under the conditions explained above, the removal of the endotoxins, β-glucans and/or peptidoglycans requires the implementation of a combination of quite particular treatment steps.

As was described above, this combination of steps consists:

of the use of a specific enzyme of lysozyme or laminarinase type, for degrading the endotoxins, β-glucans and peptidoglycans, in order to significantly reduce the size thereof, of the ultrafiltration step, for removing the enzymatic fraction and retaining the impurities introduced by the industrial enzymes themselves, of the final step of treatment with activated carbon, for absorbing all the residual small debris.

With regard to this final step of treatment with activated carbon, the Freundlich isotherm curves as established in example 2 teach that the Norit SX+ quality is the one to be used.

The following table V gives the measurement of the residual β-glucan and peptidoglycan contaminants after treatments of the batches A-5250:

with lysozyme (enzyme sold by the company Fluka, having an activity of 70 000 U/mg), or with laminarinase (enzyme sold by the company Sigma under the brand name Cytohelicase®, having an activity of 1 U/mg).

It is important to note that these enzymatic preparations are not free of contaminants.

It is thus determined that:

the Fluka lysozyme has an endotoxin level>9.6 EU/ml and a peptidoglycan level of 31 000 ng/g;

the Sigma Cytohelicase® has, for its part, an endotoxin level>9.6 EU/ml and a peptidoglycan level of 38 000 ng/g.

TABLE V

| Measurement methods | Endotoxins + β-glucans (EU/g) LAL test | Peptidoglycans (ng/g) Peptidoglycan high-sensitivity test |
|---|---|---|
| Batch "A-5250" No. 3 | 9.6 | 1882 |
| 1) Lysozyme (amount of 0.1%) 20 h of incubation | 9.6 | 1694 |
| 2) 30 kDa UF treatment Volume concentration factor = 10 Permeate | 9.6 | 639 |
| 3) Treatment with Norit SX+ activated carbon at 0.5% On the ultrafiltration permeate | <0.3 | 217 |
| Batch "A-5250" No. 5 | 9.6 | 2277 |
| 1) Cytohelicase ® amount of 0.1‰ After 20 h of incubation | 38.4 | 191 |
| 2) 30 kDa UF treatment Volume concentration factor = 10 Permeate | 0.6 | <0.3 |

TABLE V-continued

| Measurement methods | Endotoxins + β-glucans (EU/g) LAL test | Peptidoglycans (ng/g) Peptidoglycan high-sensitivity test |
|---|---|---|
| 3) Treatment with Norit SX+ activated carbon at 0.5% On the ultrafiltration permeate | <0.3 | <20 |

The results show that, for batch A-5250 which will be recovered in the ultrafiltration permeate treated with activated carbon, the prior treatment with laminarinase is much more efficient than that with lysozyme for eliminating the 13-glucans and peptidoglycans, in the sense that the lysozyme treatment even has no action on batch A-5250.

The following table VI gives the measurement of the residual endotoxin and peptidoglycan contaminants after treatments of batches B-3063.

TABLE VI

| Measurement methods | Endotoxins + β-glucans (EU/g) LAL test | Peptidoglycans (ng/g) Peptidoglycan high-sensitivity test |
|---|---|---|
| Batch "B-3063" No. 3 | 9.6 | 27 260 |
| 1) Lysozyme (amount of 0.1%) 20 h of incubation | 2.4 | 4467 |
| 2) 30 kDa UF treatment Volume concentration factor = 10 Permeate | 1.2 | 30 |
| 3) Treatment with Norit SX+ activated carbon at 0.5% On the ultrafiltration permeate | <0.3 | <20 |
| Batch "B-3063" No. 5 | 2.4 | 55 691 |
| 1) Cytohelicase ® amount of 0.1‰ After 20 h of incubation | 4.8 | 185 |
| 2) 30 kDa UF treatment Volume concentration factor = 10 Permeate | <0.3 | <20 |
| 3) Treatment with Norit SX+ activated carbon at 0.5% On the ultrafiltration permeate | <0.3 | <20 |

The results show that, for batch B-3063 which will be recovered in the ultrafiltration permeate treated with activated carbon, the prior treatment with laminarinase is much more efficient than that with lysozyme for eliminating the peptidoglycans.

The following table VII gives the measurement of the residual β-glucan/endotoxin and peptidoglycan contaminants after treatment of batches C.

TABLE VII

| Measurement methods | Endotoxins + β-glucans (EU/g) LAL test | Peptidoglycans (ng/g) Peptidoglycan high-sensitivity test |
|---|---|---|
| Batch "C" No. 3 | 9.6 | 10 556 |
| 1) Lysozyme (amount of 0.1%) 20 h of incubation | 9.6 | 17 968 |
| 2) 30 kDa UF treatment Volume concentration factor = 10 Permeate | 9.6 | 534 |
| 3) Treatment with Norit SX+ activated carbon at 0.5% On the ultrafiltration permeate | <0.3 | 20 |
| Batch "C" No. 5 | 9.6 | 11 920 |
| 1) Cytohelicase ® amount of 0.1‰ After 20 h of incubation | 4.8 | 1293 |

TABLE VII-continued

| Measurement methods | Endotoxins + β-glucans (EU/g) LAL test | Peptidoglycans (ng/g) Peptidoglycan high-sensitivity test |
|---|---|---|
| 2) 30 kDa UF treatment Volume concentration factor = 10 Permeate | <0.3 | 76 |
| 3) Treatment with Norit SX+ activated carbon at 0.5% On the ultrafiltration permeate | <0.3 | <20 |

The results show that, for batch C which will be recovered in the ultrafiltration permeate treated with activated carbon, the prior treatment with laminarinase is much more efficient than that with lysozyme for eliminating the endotoxins/β-glucans and peptidoglycans, in the sense that the lysozyme treatment even has no action on batch A-5250.

These results demonstrate that the choice of the enzyme for degrading the cell walls is not trivial here and indeed depends on the nature of the contaminants present in these various batches.

The treatment with Cytohelicase® will clearly be preferable to that with lysozyme.

EXAMPLE 4

Treatment by Ultrafiltration then Activated Carbon

As will be demonstrated, in certain situations, treatment by ultrafiltration alone can enable entirely satisfactory reduction of the endotoxins, β-glucans and peptidoglycans.

The method is carried out in the same way as that described in example 3, but without the use of enzymes (and therefore without modification of the pH and of the temperature).

4.1 Treatment on a Batch A-5250

Table VIII gives the content of residual β-glucan and peptidoglycan contaminants after each step, for batch A-5250 No. 4.

TABLE VIII

| Measurement methods | Endotoxins + β-glucans (EU/g) LAL test | Peptidoglycans (ng/g) Peptidoglycan high-sensitivity test |
|---|---|---|
| Batch "A-5250" No. 4 | 4.8 | 3166 |
| 1) UF 30 kDa UF treatment Volume concentration factor = 10 Permeate | 4.8 | 883 |
| 2) Treatment with Norit SX+ activated carbon at 0.5% On the ultrafiltration permeate | <0.3 | <20 |

The combination of the ultrafiltration and activated carbon finishing steps makes it possible to guarantee decontamination of the starch hydrolysates of batch A-5250.

If a comparison is made with the values of the method of table V (other than the values obtained with the lysozyme treatment), it is, however, noted that the reduction in β-glucans and peptidoglycans is better if the treatment with Cytohelicase® is carried out before the ultrafiltration step, even though, after the finishing treatment with Norit SX+ activated carbon, the results are identical.

This prior treatment with Cytohelicase® is therefore to be recommended for optimizing the efficiency of the decontamination treatment (capability of the decontamination method in accordance with the invention, i.e. its ability to accurately and repeatably produce starch hydrolysates from which its contaminants have been removed).

4.2 Treatment on a Batch B-3063

Table IX gives the content of residual endotoxin and peptidoglycan contaminants after each step, for batch B-3063 No. 4.

TABLE IX

| Measurement methods | Endotoxins + β-glucans (EU/g) LAL test | Peptidoglycans (ng/g) Peptidoglycan high-sensitivity test |
|---|---|---|
| Batch "B-3063" No. 4 | 1.2 | 10 241 |
| 1) 30 kDa UF treatment Volume concentration factor = 10 Permeate | 1.2 | <20 |
| 2) Treatment with Norit SX+ activated carbon at 0.5% On the ultrafiltration permeate | <0.3 | <20 |

The combination of the ultrafiltration and finishing activated carbon steps makes it possible to guarantee decontamination of the starch hydrolysates of batch B-3063.

If a comparison is made with the values of the method of table VI (other than the values obtained with the lysozyme treatment), it is, however, noted that the reduction in endotoxins and peptidoglycans is also better if the treatment with Cytohelicase® is carried out before the ultrafiltration step, even though, after the finishing treatment with Norit SX+ activated carbon, the results are identical.

4.3 Treatment on a Batch C

Table X gives the content of residual endotoxins and peptidoglycan contaminants after each step, for batch C No. 4.

TABLE X

| Measurement methods | Endotoxins + β-glucans (EU/g) LAL test | Peptidoglycans (ng/g) Peptidoglycan high-sensitivity test |
|---|---|---|
| Batch C No. 4 | 4.8 | 9353 |
| 1) 30 kDa UF treatment Volume concentration factor = 10 Permeate | 38.4 | 340 |
| 2) Treatment with Norit SX+ activated carbon at 0.5% On the ultrafiltration permeate | <0.3 | <20 |

The combination of the ultrafiltration and finishing activated carbon steps makes it possible to guarantee decontamination of the starch hydrolysates of batch C.

If a comparison is made with the values of the method of table VII (other than the values obtained with the lysozyme treatment), it is, however, noted that the reduction in endotoxins/β-glucans and peptidoglycans is also better if the treatment with Cytohelicase® is carried out before the ultrafiltration step, even though, after the finishing treatment with Norit SX+ activated carbon, the results are identical.

EXAMPLE 5

Method for Decontaminating the Starch Hydrolysate Using a Succession of Activated Carbon Steps Batches "A-5250" No. 6; "B-3063" No. 6 and "C" No. 6 from which the contaminating microorganisms have been removed in the manner as described in example 3, are subjected to the following treatments.

5.1. Two Treatments in Series with an Activated Carbon of the Same Quality

This involves applying a double treatment with the same activated carbon, in the case in point Norit SX+ at 0.25% on a dry basis, characteristic of a treatment of "micropore" type.

The following table XI gives the results obtained. As a control, a single treatment with activated carbon with a double amount of Norit SX+ is also carried out.

TABLE XI

| Starch hydrolysate | | Endotoxins + β-glucans (EU/g) | Peptidoglycans (ng/g) |
|---|---|---|---|
| Batch "A-5250" No. 6 | start | 9.6 | 3540 |
| | 1st TN | 2.4 | 593 |
| | 2nd TN | <0.3 | <10 |
| | "double amount" TN | 0 | 60 |
| Batch "B-3063" No. 6 | start | 2.4 | 46 367 |
| | 1st TN | <0.3 | 223 |
| | 2nd TN | <0.3 | <10 |
| | "double amount" TN | <0.3 | 76 |
| Batch "C" No. 6 | start | 9.6 | 16 288 |
| | 1st TN | <0.3 | 80 |
| | 2nd TN | <0.3 | <10 |
| | "double amount" TN | <0.3 | 14 |

It is clearly apparent that a two-step treatment with activated carbon is more efficient than a single treatment with a double amount, especially for removing peptidoglycans.

5.2. Two Treatments in Series with Activated Carbon of Different Quality

First treatment: Chemical carbon: ENO-PC from Norit at 0.25% of "mesopore" type;

Second finishing treatment: Norit SX+ at 0.25%, of "micropore" type.

The following table XII gives the results obtained. As a control, a single treatment with activated carbon with a mixture of the two activated carbon qualities was also carried out (reference "mix" TN).

TABLE XII

| Starch hydrolysate | | Endotoxins + β-glucans (EU/g) | Peptidoglycans (ng/g) |
|---|---|---|---|
| Batch "A-5250" | start | 9.6 | 3540 |
| | 1st TN | 0.6 | 299 |
| | 2nd TN | <0.3 | <10 |
| | "mix" TN | <0.3 | 37 |
| Batch "B-3063" | start | 2.4 | 46 367 |
| | 1st TN | <0.3 | 1096 |
| | 2nd TN | <0.3 | <10 |
| | "mix" TN | <0.3 | 91 |
| Batch "C" | start | 9.6 | 16 228 |
| | 1st TN | 1.2 | 777 |
| | 2nd TN | <0.3 | 11 |
| | "mix" TN | <0.3 | 68 |

It is also apparent here that a two-step treatment is more efficient than a single-step treatment, mixing the two activated carbon qualities.

For batch A-5250, it is apparent that the first mesopore treatment enables a more efficient reduction than the micropore treatment, providing finishing by micropore treatment which guarantees a level of contaminants below the threshold of quantification of the conventional assaying methods (in accordance with the teaching of example 2).

For batches 3063 and C, as had been found in example 2: a double treatment with the Norit SX+ "micropore" quality is the most efficient.

The invention claimed is:

1. A method for decontaminating starch hydrolysates from which glucose polymers for producing peritoneal dialysis solutions will be prepared, said method comprising:
    a) preparing a starch hydrolysate,
    b) filtering said starch hydrolysate so as to remove any contaminant having the size of a yeast, mold or bacterium,
    c) treating said starch hydrolysate so as to remove any contaminant having the minimum size of 50 Angstroms by means of a technique selected from the group consisting of activated carbon of "mesopore" type, activated carbon of "micropore" type, frontal microfiltration and tangential ultrafiltration,
    d) treating the resulting starch hydrolysate on activated carbon with a high adsorption capacity, and
    e) collecting the decontaminated starch hydrolysate.

2. The method of claim 1, wherein the starch hydrolysate of step a) is prepared by enzymatic or chemical hydrolysis of starch so as to achieve a dextrose equivalent (DE) of less than 20.

3. The method of claim 1, wherein the starch hydrolysate of step a) is prepared by acid hydrolysis of a waxy starch milk to give a DE between 8 and 15 and optionally by enzymatic hydrolysis using a bacterial alpha-amylase to give a DE between 11 and 18.

4. The method of claim 1, wherein the step of removing any contaminant having the size of a yeast, mold or bacterium is performed by microfiltration or ultrafiltration.

5. The method of claim 4, wherein the microfiltration step consists of a membrane filtration where the pore diameter is 0.22 µm, optionally preceded by a membrane filtration where the pore diameter is 0.45 µm.

6. The method of claim 4, wherein the ultrafiltration step consists of a membrane of ultrafiltration where the cut-off threshold is 300,000 Da.

7. The method of claim 1, wherein said activated carbon is activated carbon of "mesopore" type.

8. The method of claim 1, wherein the tangential ultrafiltration step consists of a membrane ultrafiltration where the cut-off threshold is from 20,000 Da to 50,000 Da.

9. The method of claim 1, wherein said treating with activated carbon with a high adsorption capacity consists of activated carbon of "micropore" type.

10. The method according to claim 1, wherein said starch hydrolysate is treated with activated carbon of "mesopore" type so as to remove any contaminant having the minimum size of 50 Angstroms.

11. The method according to claim 1, wherein said starch hydrolysate is treated with activated carbon of "micropore" type so as to remove any contaminant having the minimum size of 50 Angstroms.

12. The method according to claim 1, wherein said starch hydrolysate is treated with frontal microfiltration so as to remove any contaminant having the minimum size of 50 Angstroms.

13. The method according to claim 1, wherein said starch hydrolysate is treated with tangential ultrafiltration so as to remove any contaminant having the minimum size of 50 Angstroms.

14. A method for decontaminating starch hydrolysates from which glucose polymers for producing peritoneal dialysis solutions will be prepared comprising:
    a) preparing a starch hydrolysate,
    b) filtering said starch hydrolysate so as to remove any contaminant having the size of a yeast, mold or bacteria type,
    c) treating said starch hydrolysate from which the contaminating microorganisms have thus been removed with enzymes selected from the group consisting of lysozyme and laminarinase for degrading the cell wall polysaccharide constituents, chosen laminarinase or lysozyme,
    d) ultrafiltering the enzymatically treated starch hydrolysate,
    e) treating the resulting starch hydrolysate on activated carbon with a high adsorption capacity, and
    f) collecting the starch hydrolysate thus decontaminated.

15. The method of claim 14, wherein the starch hydrolysate of step a) is prepared by enzymatic or chemical hydrolysis of starch so as to achieve a dextrose equivalent (DE) of less than 20.

16. The method of claim 14, wherein the starch hydrolysate of step a) is prepared by acid hydrolysis of a waxy starch milk to give a DE between 8 and 15and optionally by enzymatic hydrolysis using a bacterial alpha-amylase to give a DE between 11 and 18.

17. The method of claim 14, wherein step b) is carried out by microfiltration or ultrafiltration.

18. The method of claim 17, wherein the microfiltration step consists of a membrane filtration where the pore diameter is 0.22 µm, optionally preceded by a membrane filtration where the pore diameter is 0.45 µm.

19. The method of claim 17, wherein the ultrafiltration step consists of a membrane ultrafiltration where the cut-off threshold is 300,000 Da.

20. The method of claim 14, wherein the enzymatic hydrolysis treatment is carried out at the enzyme concentration of 0.001% to 1% by weight of starch hydrolysates.

21. The method of claim 14, wherein the ultrafiltration step d) consists of a membrane ultrafiltration where the cut-off threshold is from 20,000 Da to 50,000 Da.

22. The method of claim 14, wherein the step of treating with activated carbon with a high adsorption capacity consists of a quality of activated carbon of "micropore" type.

* * * * *

UNITED STATES PATENT AND TRADEMARK OFFICE
CERTIFICATE OF CORRECTION

| | | |
|---|---|---|
| PATENT NO. | : 8,933,219 B2 | Page 1 of 1 |
| APPLICATION NO. | : 13/883334 | |
| DATED | : January 13, 2015 | |
| INVENTOR(S) | : Pierrick Duflot, Damien Passe and Jean-Marc Verrin | |

It is certified that error appears in the above-identified patent and that said Letters Patent is hereby corrected as shown below:

In the specification

Column 21,
Lines 14-15, "the 13-glucans" should read --the β-glucans--.

Signed and Sealed this
Thirteenth Day of October, 2015

Michelle K. Lee
*Director of the United States Patent and Trademark Office*